United States Patent
Ihn et al.

(10) Patent No.: US 8,499,632 B1
(45) Date of Patent: Aug. 6, 2013

(54) CHARACTERIZING ANOMALIES IN A LAMINATE STRUCTURE

(75) Inventors: Jeong-Beom Ihn, Bellevue, WA (US); Justin Kearns, Seattle, WA (US)

(73) Assignee: The Boeing Company, Chicago, IL (US)

( * ) Notice: Subject to any disclaimer, the term of this patent is extended or adjusted under 35 U.S.C. 154(b) by 304 days.

(21) Appl. No.: 12/861,076

(22) Filed: Aug. 23, 2010

(51) Int. Cl.
*G01N 29/024* (2006.01)

(52) U.S. Cl.
USPC ............... 73/587; 73/597; 73/598; 73/602

(58) Field of Classification Search
USPC .............. 73/587, 579, 580, 597, 602, 620, 73/622, 627, 801; 702/56, 183, 184, 185, 702/188
See application file for complete search history.

(56) References Cited

U.S. PATENT DOCUMENTS

| | | | |
|---|---|---|---|
| 4,187,725 A | 2/1980 | Gavrev et al. | |
| 4,299,128 A | 11/1981 | Gruber | |
| 4,546,652 A | 10/1985 | Virkar et al. | |
| 4,574,637 A | 3/1986 | Adler et al. | |
| 4,658,649 A | 4/1987 | Brook | |
| 4,674,334 A * | 6/1987 | Chimenti et al. | 73/627 |
| 4,817,016 A | 3/1989 | Thompson et al. | |
| 5,184,516 A | 2/1993 | Blazic et al. | |
| 5,760,904 A | 6/1998 | Lorraine et al. | |
| 5,841,031 A | 11/1998 | Chung | |
| 5,932,806 A * | 8/1999 | Rose et al. | 73/599 |
| 5,987,994 A | 11/1999 | Maltby et al. | |
| 6,128,092 A | 10/2000 | Levesque et al. | |
| 6,295,247 B1 * | 9/2001 | Khuri-Yakub et al. | 367/140 |
| 6,311,565 B1 | 11/2001 | Hinz et al. | |
| 6,772,638 B2 | 8/2004 | Matney et al. | |
| 6,923,067 B2 * | 8/2005 | Coen et al. | 73/627 |
| 7,024,315 B2 | 4/2006 | Giurgiutiu | |
| 7,171,854 B2 * | 2/2007 | Nagashima et al. | 73/622 |
| 7,231,304 B2 | 6/2007 | Mitchell | |
| 7,263,888 B2 | 9/2007 | Barshinger et al. | |
| 7,333,898 B2 | 2/2008 | Griess et al. | |
| 7,367,236 B2 | 5/2008 | Georgeson et al. | |
| 7,387,033 B2 * | 6/2008 | Qing et al. | 73/862.046 |

(Continued)

FOREIGN PATENT DOCUMENTS

| | | |
|---|---|---|
| JP | 2001215218 A2 | 8/2001 |
| JP | 2005300274 | 10/2005 |
| WO | 2006/009669 A1 | 1/2006 |

OTHER PUBLICATIONS

European Patent Office, International Search Report and The Written Opinion of the International Searching Authority for International Application No. PCT/US2008/063639, dated Nov. 10, 2008.

(Continued)

*Primary Examiner* — J M Saint Surin
(74) *Attorney, Agent, or Firm* — Charles L. Moore; Moore & Van Allen PLLC

(57) ABSTRACT

A method for inspecting a laminate structure may include transmitting a lamb wave through a selected portion of the laminate structure from an actuator at a predetermined location on a surface of the laminate structure. The method may also include receiving the transmitted lamb wave at a sensor at another predetermined location on the surface of the laminate structure. The method may additionally include detecting and characterizing an anomaly in the laminate structure based on the received lamb wave.

18 Claims, 5 Drawing Sheets

U.S. PATENT DOCUMENTS

| | | | |
|---|---|---|---|
| 7,388,365 | B2 | 6/2008 | Nokuo et al. |
| 7,434,480 | B2 * | 10/2008 | Georgeson et al. ...... 73/862.041 |
| 7,458,266 | B2 * | 12/2008 | Beard et al. ............ 73/579 |
| 7,487,059 | B2 * | 2/2009 | Davis et al. ............ 702/116 |
| 7,552,027 | B2 | 6/2009 | Kearns et al. |
| 7,891,247 | B2 * | 2/2011 | Ihn ............... 73/602 |
| 2004/0206181 | A1 | 10/2004 | Coen et al. |
| 2005/0068041 | A1 | 3/2005 | Kress et al. |
| 2007/0017297 | A1 * | 1/2007 | Georgeson et al. ......... 73/801 |
| 2008/0283332 | A1 | 11/2008 | Ihn |
| 2009/0032329 | A1 | 2/2009 | Ihn |
| 2009/0157358 | A1 * | 6/2009 | Kim ............... 702/185 |
| 2010/0217544 | A1 * | 8/2010 | Yan et al. ............ 702/56 |
| 2011/0231112 | A1 * | 9/2011 | Soejima et al. ............ 702/35 |

OTHER PUBLICATIONS

European Patent Office, International Search Report and The Written Opinion of the International Searching Authority for International Application No. PCT/US2009/036188, dated Mar. 22, 2010.

Kress, K.-P., "Smart Wide-area Imaging Sensor System (SWISS)." Proceedings of the SPIE—The Intern a it on al Society for Optical Engineering, SPIE, US, vol. 4332 (2001):490-496.

* cited by examiner

CHARACTERIZING ANOMALIES IN A LAMINATE STRUCTURE

FIELD

The present disclosure relates to non-destructive inspection of structures or parts, and more particularly to a system and method for characterizing or evaluating anomalies, such as wrinkles, in a laminate structure, such as a composite structure or similar structure.

BACKGROUND

New, lightweight composite materials and designs are being used more extensively in the aerospace industry for commercial aircraft and other aerospace vehicles, as well as in other industries. The structures using these composite materials may be formed using multiple plies or layers of material that may be laminated together to form a lightweight, high strength structure. Variances in the cure process of complex composite structures with tight curvatures, such as for example stringers in an aircraft or other curved structures, can result in wrinkles of varying degrees of size. These wrinkles may cause structural degradation of the part. The structural degradation may vary based on the size of the wrinkle. Quality assurance and certification for production parts in industries, such as the aircraft industry requires that the part be built to meet certain design standards and specifications. For some parts there may be a standard acceptance criteria based on wrinkle size. Accordingly being able to accurately detect and measure the size of any wrinkles in a structure or part is desirable. One technique and system 100 for non-destructive inspection (NDI) is illustrated in FIG. 1. The system 100 includes a NDI transducer 102 for generating an ultrasonic B-scan or bulk wave (illustrated by arrow 104 in FIG. 1) in response to an electrical signal from an NDI monitoring device 106 or inspection device connected to the NDI transducer 102. The NDI transducer 102 transmits the bulk wave 104 substantially perpendicular into a surface 108 of the laminate structure 110 for the bulk wave 104 to pass through a thickness of the structure 110 to an opposite side 112 of the structure 110. An arrival time of a pulse echo wave (illustrated by arrow 114 in FIG. 1) sooner than an expected reflection off an opposite side 112 of the laminate structure 110 may indicate an anomaly, such as a delamination and wrinkle. The arrival time of the pulse echo wave 114 may be measured by the NDI monitoring unit 106. While the system 100 may detect the presence of an anomaly or delamination, correlating wrinkle sizes, specifically those with larger heights, with a high degree of accuracy may be difficult using through-thickness bulk waves or B-scan waves as illustrated in FIG. 1.

SUMMARY

In accordance with an embodiment, a method for inspecting a laminate structure may include propagating ultrasonic lamb waves or stress waves through a composite structure from one piezoelectric transducer to another piezoelectric transducer or between multiple transducers. Characteristics of the lamb waves, such as a wave group velocity, may be used to determine the anomaly or wrinkle size and shape. The wave group velocity relates to overall stiffness and strength reduction of the structure. The method takes advantage of the changes in the in-plane ultrasonic lamb wave group velocity due to a wrinkle. A wrinkle, depending on the size, changes the localized laminate bulk properties. The wave group velocity is directly proportional to the square root of the bulk laminate modulus divided by the density. Therefore, if a lamb wave is propagated through the wrinkled zone of the structure, the group velocity will be lower as compared to a healthy region. Furthermore, the group velocity will also vary according to the size of the wrinkle as wrinkle size has been correlated to proportional reductions in modulus.

In accordance with another embodiment, a method for inspecting a laminate structure may include transmitting a lamb wave through a selected portion of the laminate structure from an actuator at a predetermined location on a surface of the laminate structure. The method may also include receiving the transmitted lamb wave at a sensor at another predetermined location on the surface of the laminate structure. The method may additionally include detecting and characterizing an anomaly in the laminate structure based on the received lamb wave.

In accordance with another embodiment, a method for inspecting a laminate structure may include transmitting a stress wave through a selected portion of the laminate structure from an actuator at a predetermined location on a surface of the laminate structure. The method may also include receiving the transmitted lamb wave at a sensor at another predetermined location on the surface of the laminate structure. The method may further include correlating a speed of the stress wave from the actuator to the sensor to a modulus of the laminate structure to detect any anomalies in the laminate structure.

In accordance with a further embodiment, a system for inspecting a laminate structure may include an actuator on a surface of the laminate structure to transmit a lamb wave through the laminate structure and a sensor on a surface of the laminate structure to receive the transmitted lamb wave. The system may also include a device for detecting and characterizing an anomaly in the laminate structure based on the received lamb wave.

Other aspects and features of the present disclosure, as defined solely by the claims, will become apparent to those ordinarily skilled in the art upon review of the following non-limited detailed description of the disclosure in conjunction with the accompanying figures.

BRIEF DESCRIPTION OF THE SEVERAL VIEWS OF THE DRAWINGS

The following detailed description of embodiments refers to the accompanying drawings, which illustrate specific embodiments of the disclosure. Other embodiments having different structures and operations do not depart from the scope of the present disclosure.

DESCRIPTION

The following detailed description of embodiments refers to the accompanying drawings, which illustrate specific embodiments of the disclosure. Other embodiments having different structures and operations do not depart from the scope of the present disclosure.

Figure 1:
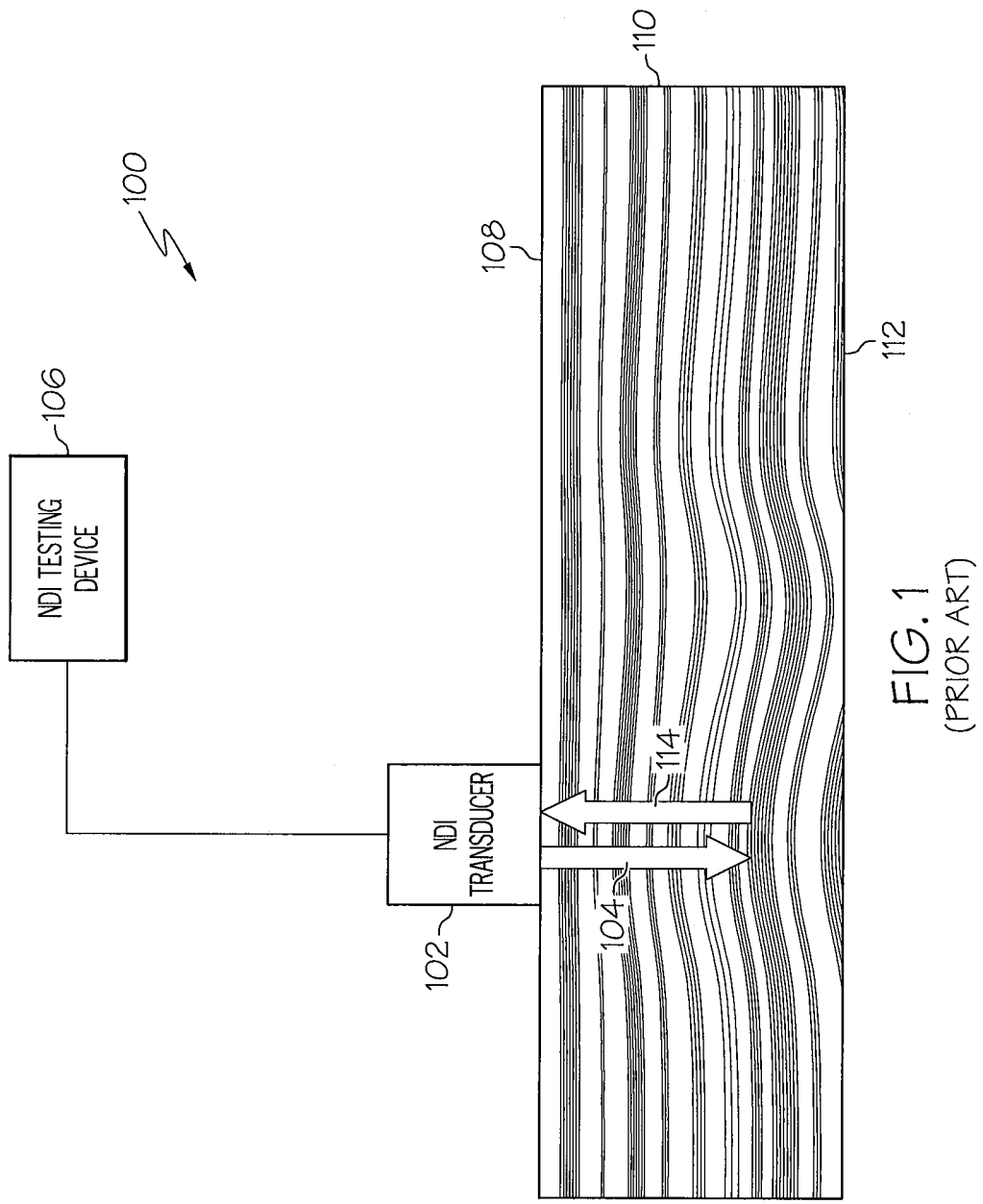
FIG. 1 is a block diagram of an example of a conventional non-destructive inspection (NDI) system for generating and transmitting bulk waves perpendicular into the surface of a structure under inspection.
Figure 2:
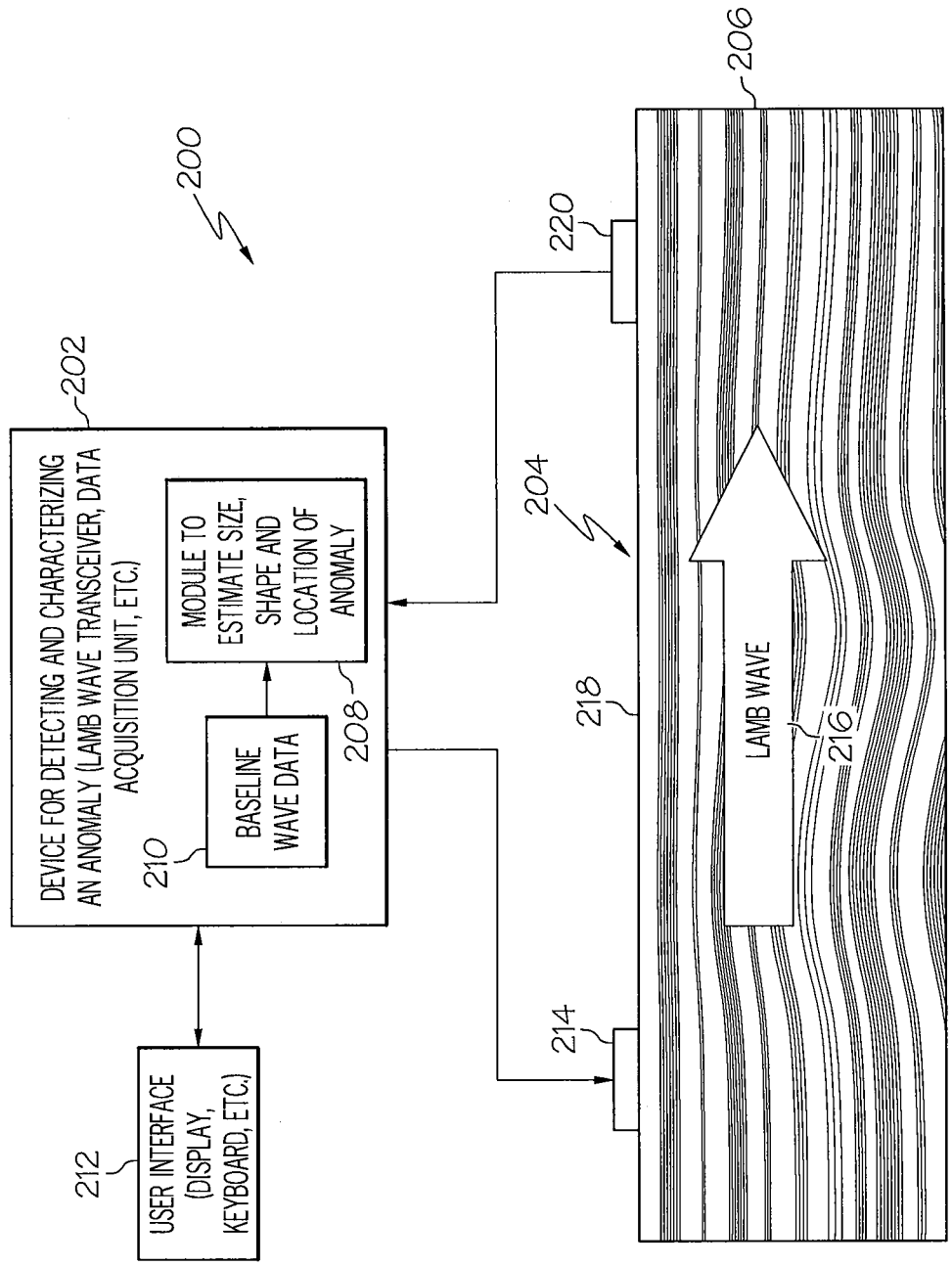
FIG. 2 is a block schematic diagram of an example of a NDI system for detecting and characterizing anomalies in accordance with an embodiment of the present disclosure.

FIG. 2 is a block schematic diagram of an example of a NDI system 200 for detecting and characterizing anomalies in accordance with an embodiment of the present disclosure. The system 200 may include a device 202 for detecting and characterizing an anomaly similar to that described herein. Characterizing the anomaly may include determining or estimating a size, shape and location of the anomaly. An anomaly may be any wrinkle or other defect in a laminated structure. Similar to that previously described, a wrinkle in a laminated structure or part can cause structural degradation of the laminated structure or part which can vary based on the size of the wrinkle.

The device 202 for detecting and characterizing an anomaly may include a lamb wave transceiver, a data acquisition unit and similar components for generating lamb waves and receiving resulting waveform signals or data resulting from a received lamb wave which has been transmitted through a selected portion 204 of a laminate structure 206. The structure 206 may be a component or part of an aircraft or aerospace vehicle, terrestrial vehicle, watercraft, civil structure or other type of structure. The device 202 may include a module 208 to estimate the size, shape and location of the anomaly similar to that described herein. The device 202 may also store baseline wave data 210 for comparison to the received waveform data for determining whether or not the laminate structure 204 or part is acceptable. A user interface 212 may also be provided for controlling operation of the device 202 and providing inspection results. The user interface 212 may include a display, keyboard, computer pointing device, input and output device or devices or combination input/output devices or other components for use in operating and controlling the device 202 for detecting and characterizing an anomaly and for performing the functions and operations described herein.

The system 200 may also include an actuator 214 to generate and transmit a lamb wave 216 or stress wave through the selected portion 204 of the laminate structure 206 in response to a signal or signal waveform from the device 202 or lamb wave transmitter. The actuator 214 may be located at a predetermined location on a surface 218 of the laminate structure 206. The lamb wave 216 may be an ultrasonic lamb wave 216 that is transmitted in-plane or substantially parallel to the surface 218 of the laminate structure 206. The in-plane lamb wave 216 may be transmitted from the actuator 214 to a sensor 220. The sensor 220 may be at another predetermined location on the surface 218 of the laminate structure 206 to inspect the selected portion 204 of the laminate structure 206.

The actuator 214 and the sensor 220 may each be a piezoelectric transducer mounted or mechanically attached or coupled to the surface 218 of the laminated structure 206. The selected portion 204 of the laminate structure 206 under inspection may be defined as the region between the actuator 214 and the sensor 220. The actuator 214 may be electronically excited and will mechanically strain because of the inherent electromechanical coupling of the actuator 214 to the surface 218 of the laminate structure 206. An ultrasonic plane stress wave (lamb wave) 216 is emitted through the laminate structure 206 in response to the electronic excitation of the actuator 214 and the mechanical strain. The sensor 220 mechanically strains as the wavefront of the lamb wave 216 propagates and reaches the sensor 220. The sensor 220 may output an electrical signal to the data acquisition system or device 202 for detecting and characterizing any anomalies or wrinkles in the selected portion 204 of the laminate structure 206.

The inherent nature of plate dynamics causes dispersion, or a change in group velocity of the transmitted lamb wave 216 as a function of frequency and a thickness of the laminate structure 206 or part. Therefore, depending on the operational frequency at which the lamb waves are generated in the laminate structure 206, different and many modes may participate or be created. The ideal situation exists when there is clear separation between modes. For a unique structure thickness, there may be a range of frequencies that such separation between modes exists. For example, there may be two modes present at a particular frequency of excitation of the actuator 214 and thickness of material of the laminate structure 206. For inspection applications the two modes may be the fundamental symmetric mode (s0) and fundamental asymmetric mode (a0). Since the two modes are traveling at two different speeds and may have different amplitudes or attenuation rate per distance, a measured response from the sensor 220 may show the two modes overlapped in time or separated in time depending on the spacing between the actuator 214 and sensor 220, operation, frequency, and any other parameters that may effect the modes. For data analysis, it will be best if one mode can be captured separated from any other and to see how properties of the mode (i.e. group velocity) changes due to presence of an anomaly, such as a wrinkle. If the mode of interest is overlapped with other modes in time, a mode decomposition process will need to be performed to separate the modes and their separation. Mode separation takes additional computational efforts. An easier process is to change the frequency at which the lamb wave is generated until there is a natural mode separation in time between the modes and use that frequency for generating the lamb waves for inspection.

Figure 4:
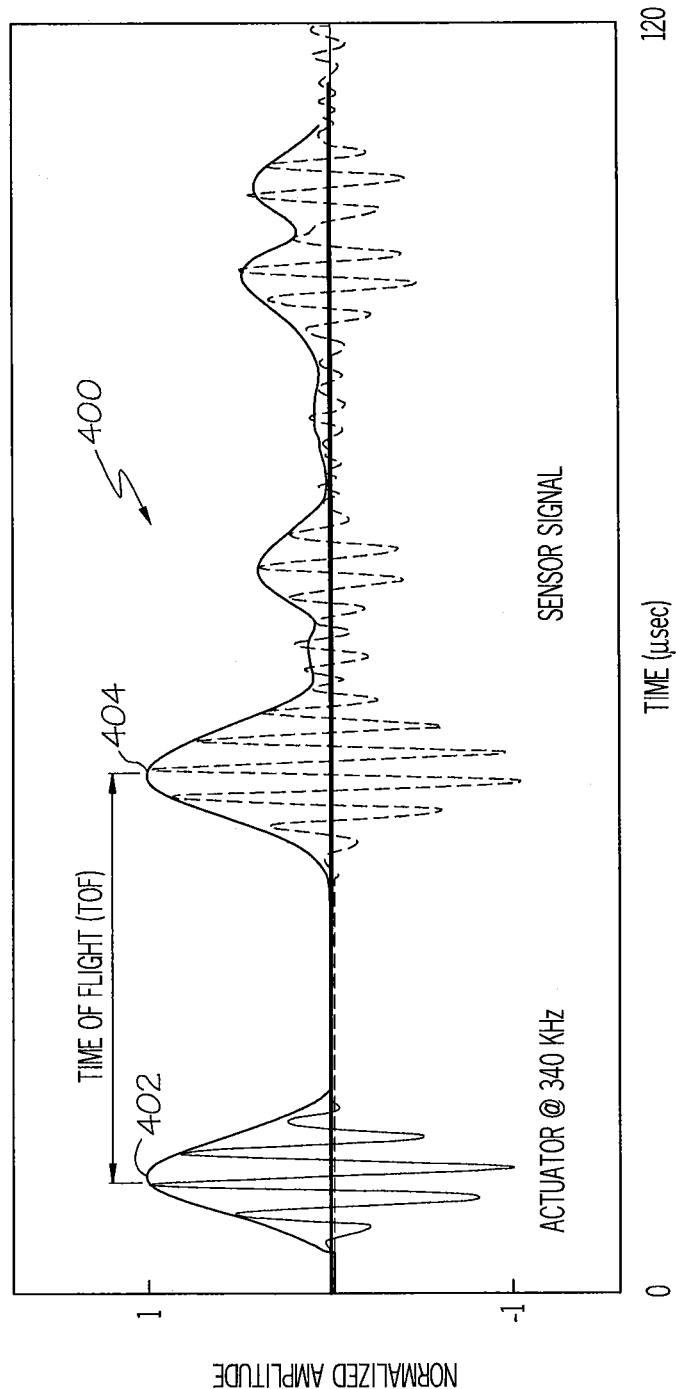
FIG. 4 is an illustration of a processed signal waveform for determining group velocity in accordance with an embodiment of the present disclosure.

The group velocity may then be measured for each wave packet by the ratio of the distance between the actuator 214 and the sensor 220, and the time of flight or time for the wavefront of the lamb wave 216 to propagate from the actuator 214 to the sensor 220. The group velocity is directly proportional to laminate bulk modulus and density. FIG. 4 is an illustration of a processed signal waveform 400 that may be generated from sensor 220 in response to receiving the transmitted lamb wave 216 for determining group velocity in accordance with an embodiment of the present disclosure. The time of flight may be determined as the time from when the lamb wave 208 is transmitted by the actuator 214 at reference point 402 in FIG. 4 to the reference point 404 in the waveform 400 when the sensor 220 receives the lamb wave 216.

Figure 3:
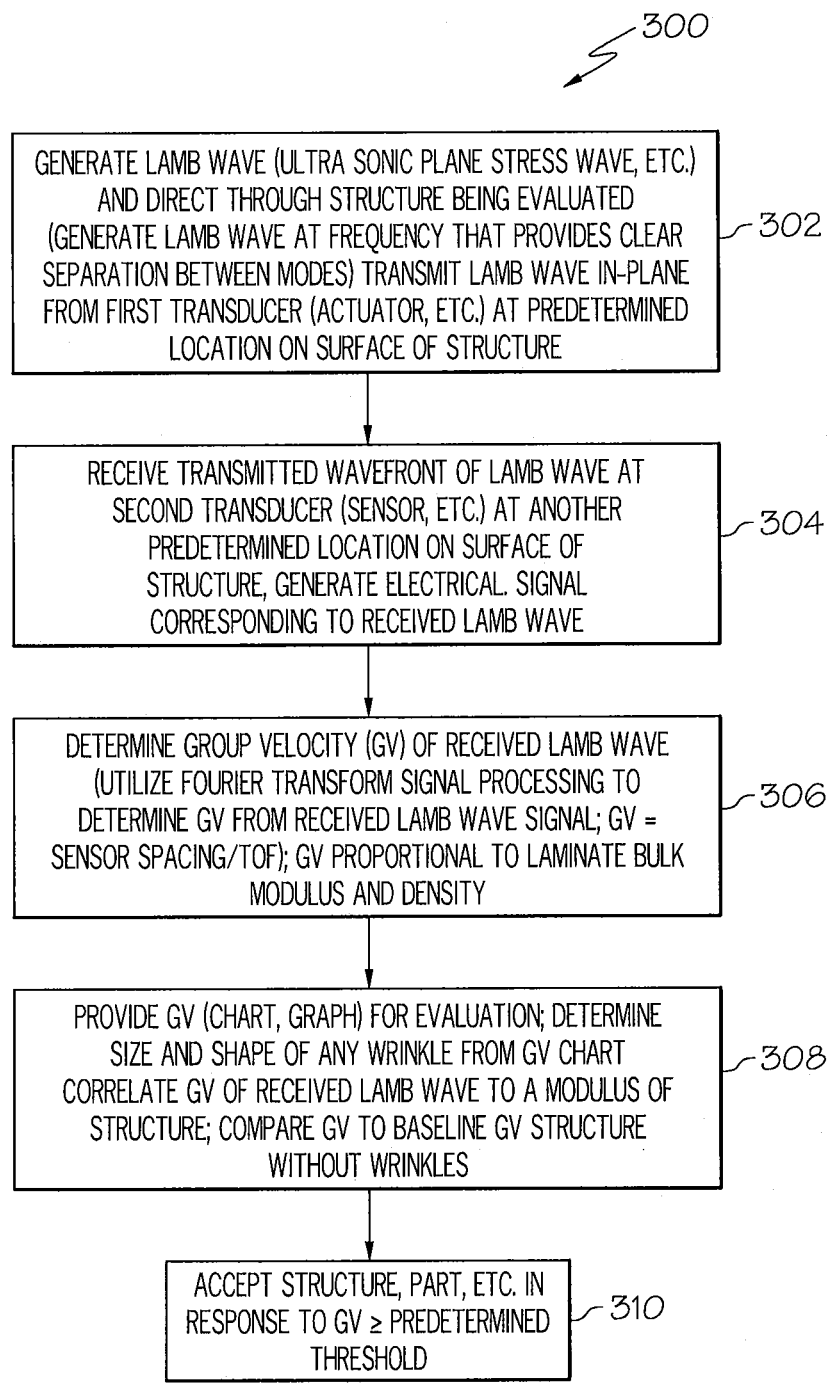
FIG. 3 is an example of a method for detecting and characterizing anomalies in accordance with an embodiment of the present disclosure.

FIG. 3 is an example of a method 300 for detecting and characterizing anomalies in accordance with an embodiment of the present disclosure. The method 300 may be embodied in the device 202 or module 208 to estimate the size and shape and location of an anomaly in FIG. 2. In block 302, a lamb wave may be generated and directed through the structure being evaluated or inspected. As previously discussed, the lamb wave may be an ultrasonic plane stress wave or similar electromagnetic energy. The lamb wave may be generated at a frequency that provides clear separation between the modes as previously discussed. The lamb wave may be transmitted in-plane, or substantially parallel to a surface of the structure being inspected, from a first transducer or actuator at a predetermined location on the surface of the structure under test.

In block 304, the transmitted wavefront of the lamb wave may be received at a second transducer or sensor at another predetermined location on the surface of the structure. An electrical signal corresponding to the received lamb wave may be generated by the transducer.

In block 306, a group velocity may be determined from the received lamb wave. Fourier transform signal processing or similar signal processing may be utilized to determine the group velocity from the electrical signal corresponding to the lamb wave signal received by the transducer or sensor, such as sensor 220 and FIG. 2. The group velocity may be equal to the spacing between the transducers divided by the time of flight of the lamb wave. As previously described, FIG. 4 illustrates a signal waveform corresponding to the received lamb wave for determining the time of flight and group velocity. The group velocity is also directly proportional to a square root of a bulk modulus of the laminate structure provided by a density of the laminate structure.

Figure 5:
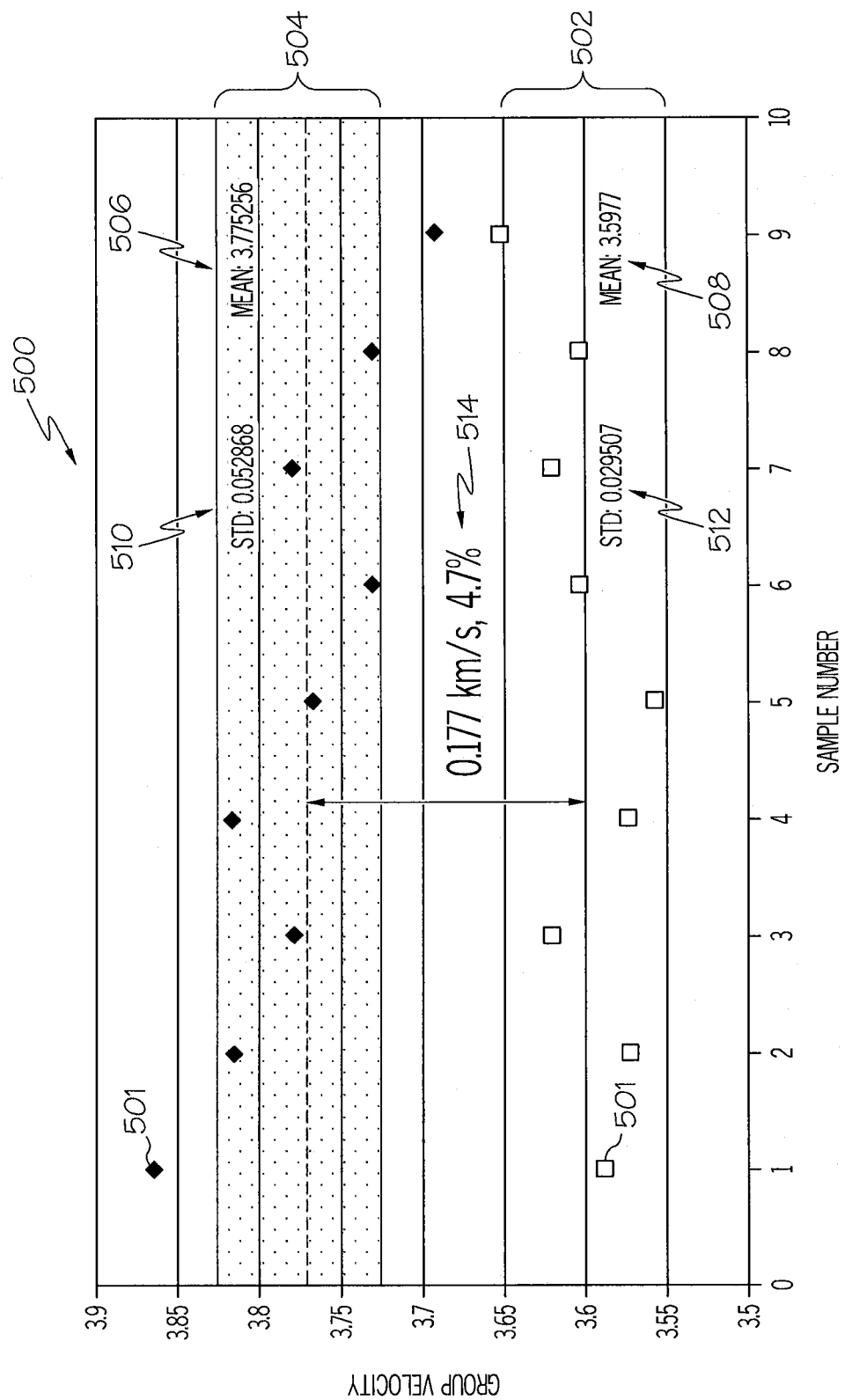
FIG. 5 is an example of a chart of group velocity measurements for multiple samples from a structure for evaluating the structure in accordance with an embodiment of the present disclosure.

In block 308, a group velocity chart may be provided for evaluation of the structure and detecting any anomalies. An example of a group velocity chart 500 is illustrated in FIG. 5 and will be described in more detail with reference to FIG. 5. A size and shape of any anomaly or wrinkle may be determined from the group velocity chart 500. The group velocity of the received lamb wave may be correlated to a modulus of the structure under inspection.

In accordance with an embodiment, lamb waves may be received at multiple sample points on the surface of the laminate structure. The location of each of the multiple sample points is known. A group velocity from the lamb wave received at each sample point may be determined. A location and size of the anomaly may be determined from the received group velocities from the different multiple sample points.

In accordance with an embodiment, the group velocity of the lamb wave may be compared to the group velocity of a baseline group velocity for a laminated structure known to not contain any anomalies or wrinkles. The laminated structure may then be accepted or rejected based on the comparison.

In block 310, the laminated structure or part may be accepted or certified in response to the group velocity being greater than a predetermined threshold value.

FIG. 5 is an example of a chart 500 of group velocity measurements 501 for multiple samples from a structure for evaluating the structure in accordance with an embodiment of the present disclosure. The group velocity chart 500 illustrates multiple samples of group velocities 501 for a structure under inspection. The group velocities 501 in a first band 502 illustrate group velocities at a much slower group velocity compared to group velocities 501 in a second band 504. For the same transducer spacing, the group velocities 501 in the first band 502 are slower because of a longer time of flight caused by an anomaly or wrinkle in the structure under inspection. A wrinkle, depending upon the size changes the localized laminate bulk properties. The wave group velocity is directly proportional to the square root of the bulk laminate modulus divided by the density of the structure. Accordingly, if a lamb wave is propagated through a wrinkle zone in the laminate structure, the group velocity will be lower, such as those group velocities in band 502, compared to a healthy region or region without any wrinkles or delaminations, such those group velocities in band 504 in FIG. 5. The group velocity may also vary according to the size of the wrinkle as wrinkle size may be correlated to proportional reductions in modulus or bulk modulus. Accordingly, the size and shape of the wrinkle may also be determined or estimated from the group velocity. A mean 506 and 508 may be determined for each band of group velocities 502 and 504 as well as a standard deviation 510 and 512 for evaluating the structure and comparing differences between a region in the structure with a wrinkle or anomaly and another region without any wrinkles or anomalies. A difference 514 between the means may be determined. The data may be used for future reference and comparison for inspecting and evaluating parts for use in a vehicle, such as an aircraft or other vehicle.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the embodiments herein have other applications in other environments. This application is intended to cover any adaptations or variations of the present disclosure. The following claims are in no way intended to limit the scope of the disclosure to the specific embodiments described herein.

What is claimed is:

1. A method for inspecting a laminate structure, comprising:
   generating a lamb wave, wherein generating the lamb wave comprises changing a frequency of the lamb wave to find the frequency that provides a natural separation between modes;
   transmitting the lamb wave at the frequency that provides the natural separation between modes and transmitting the lamb wave through a selected portion of the laminate structure from an actuator at a predetermined location on a surface of the laminate structure;
   receiving the transmitted lamb wave at a sensor at another predetermined location on the surface of the laminate structure; and
   detecting and characterizing an anomaly in the laminate structure based on the received lamb wave.

2. The method of claim 1, wherein transmitting the lamb wave comprises transmitting the lamb wave in-plane between the actuator and the sensor, wherein the lamb wave is transmitted substantially parallel to the surface of the laminate structure.

3. The method of claim 1, wherein characterizing the anomaly in the laminate structure comprises determining a size and shape of the anomaly.

4. The method of claim 1, further comprising wherein generating the lamb wave comprises generating the lamb wave to provide separation between a fundamental symmetric mode and a fundamental asymmetric mode of the lamb wave.

5. The method of claim 1, further comprising performing mode separation in response to a mode of the received lamb wave to be used for detecting and characterizing the anomaly overlapping another mode of the received lamb wave.

6. The method of claim 1, further comprising determining a group velocity of the received lamb wave, wherein the group velocity is directly proportional to a square root of a bulk modulus of the laminate structure divided by a density of the laminate structure.

7. The method of claim 6, further comprising accepting the laminate structure in response to the group velocity being greater than or equal to a preset threshold for the laminate structure.

8. The method of claim 6, wherein determining the group velocity comprises performing Fourier transform signal processing on the received lamb wave.

9. The method of claim 6, further comprising detecting and determining a size and shape of the anomaly from the group velocity of the received lamb wave, wherein the group velocity varies according to the size of the anomaly.

10. The method of claim 6, wherein determining the group velocity comprises determining a time of flight of the lamb wave from the actuator to the sensor.

11. The method of claim 10, further comprising:
providing a chart of the group velocities for each of the multiple sample points; and
determining a location and size of the anomaly from the chart of group velocities.

12. The method of claim 1, further comprising:
receiving the lamb wave at multiple sample points on the surface of the laminate structure; and
determining a group velocity from the lamb wave received at each sample point.

13. The method of claim 1, further comprising:
determining a group velocity of the lamb wave; and
comparing the group velocity of the lamb wave to the group velocity of a baseline group velocity for a laminated structure known to not contain any anomalies.

14. A method for inspecting a laminate structure, comprising:
generating a stress wave, wherein generating the stress wave comprises changing a frequency of the lamb wave to find the frequency that provides a natural separation between modes;
transmitting the lamb wave at the frequency that provides the natural separation between modes and transmitting the stress wave through a selected portion of the laminate structure from an actuator at a predetermined location on a surface of the laminate structure;
receiving the transmitted stress wave at a sensor at another predetermined location on the surface of the laminate structure; and
correlating a speed of the stress wave from the actuator to the sensor to a modulus of the laminate structure to detect any anomalies in the laminate structure.

15. The method of claim 14, further comprising characterizing a size and shape of an anomaly in the laminate structure from correlating the speed of the stress wave.

16. The method of claim 14, wherein transmitting the stress wave comprises transmitting the stress wave in-plane between the actuator and the sensor, wherein the stress wave is transmitted substantially parallel to the surface of the laminate structure.

17. A system for inspecting a laminate structure, comprising:
an actuator on a surface of the laminate structure to generate and transmit a lamb wave through the laminate structure, wherein the lamb wave is generated by changing a frequency of the lamb wave to find the frequency that provides a natural separation between modes and the lamb wave is transmitted at the frequency that provides the natural separation between modes;
a sensor on a surface of the laminate structure to receive the transmitted lamb wave; and
a device for detecting and characterizing an anomaly in the laminate structure based on the received lamb wave.

18. The system of claim 17, wherein the device for detecting and characterizing an anomaly comprises a module to determine a size and shape of the anomaly from a group velocity of the received lamb wave.

* * * * *